United States Patent
Becker et al.

(10) Patent No.: US 6,413,749 B1
(45) Date of Patent: Jul. 2, 2002

(54) GRANULE CONTAINING PROTEIN AND CORN STARCH LAYERED ON AN INERT PARTICLE

(75) Inventors: Nathaniel T. Becker, Hillsborough; Thomas S. Green, Montara, both of CA (US)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 09/428,153

(22) Filed: Oct. 27, 1999

Related U.S. Application Data

(60) Provisional application No. 60/105,874, filed on Oct. 27, 1998.

(51) Int. Cl.[7] .......................... C12N 9/98; C12N 11/02; C12N 11/10; C12N 11/04; C12N 9/96
(52) U.S. Cl. ................. 435/187; 435/177; 435/178; 435/182; 435/188
(58) Field of Search .................. 435/174, 176, 435/177, 178, 180, 182, 187, 188

(56) References Cited

U.S. PATENT DOCUMENTS

| | | | |
|---|---|---|---|
| 4,106,991 A | 8/1978 | Markussen et al. | 435/187 |
| 4,572,897 A | 2/1986 | Amotz et al. | 435/177 |
| 4,689,297 A | 8/1987 | Good et al. | 435/174 |
| 4,740,469 A | 4/1988 | Nishinaka et al. | 435/187 |
| 4,760,025 A | 7/1988 | Estell et al. | 435/222 |
| 5,324,649 A | 6/1994 | Arnold et al. | 435/187 |
| 5,739,091 A | 4/1998 | Kiesser et al. | 510/224 |
| 5,814,501 A | 9/1998 | Becker et al. | 435/174 |

FOREIGN PATENT DOCUMENTS

| | | |
|---|---|---|
| EP | 0 304 332 A2 | 2/1989 |
| EP | 0 130 756 B1 | 6/1991 |
| EP | 0 532 777 A1 | 3/1993 |
| GB | 1 377 725 A | 12/1974 |
| WO | WO 91/06637 | 5/1991 |
| WO | WO 91/09941 | 7/1991 |
| WO | WO 97/12958 | 4/1997 |
| WO | WO 97/23606 A1 | 7/1997 |
| WO | WO 99/32595 | 7/1999 |
| WO | WO 99/32612 A1 | 7/1999 |
| WO | WO 99/32613 | 7/1999 |

OTHER PUBLICATIONS

Gaertner, A.L. et al. "Development of low dust enzyme detergent granules with high storage stability", Proc. Int. Symp. Controlled Release Bioact. Mater. 25 (1998), pp. 289–290, XP–002102189.

Copy of International Search Report for PCT/US99/25459.

*Primary Examiner*—David M. Naff
(74) *Attorney, Agent, or Firm*—Janet Kaiser Castaneda

(57) ABSTRACT

Granules are prepared containing an admixture of protein and starch layered over an inert particle. Proteins include pharmaceutically important proteins such as hormones, or industrially important proteins such as enzymes including proteases, amylases, lipases and cellulases capable of hydrolyzing substrates such as stains. Inert particles include inorganic salts, sugars, sugar alcohols, small organic molecules such as organic acids or salts, and minerals such as clays or silicates. The admixture may also contain sugar such as sucrose. A ratio of corn starch to sugar much greater than 1:1 such as in a range of about 5:1 to about 15:1 is preferred. A coating layer may be between the inert particle and the admixture and/or over the admixture. Methods that may be used in preparing the granules include pan-coating, fluid-bed coating, prilling, disc granulation, spray drying, extrusion, centrifugal extrusion, spheronization, drum granulation and high shear agglomeration.

17 Claims, No Drawings

GRANULE CONTAINING PROTEIN AND CORN STARCH LAYERED ON AN INERT PARTICLE

RELATED APPLICATIONS

This application claims priority to U.S. Provisional Application No. 60/105,874, filed Oct. 27, 1998, which is incorporated herein in its entirety.

BACKGROUND OF THE INVENTION

Proteins such as pharmaceutically important proteins like hormones and industrially important proteins like enzymes are becoming more widely used. Enzymes are used in several industries including, for example, the starch industry, the dairy industry, and the detergent industry. It is well known in the detergent industry that the use of enzymes, particularly proteolytic enzymes, has created industrial hygiene concerns for detergent factory workers, particularly due to the health risks associated with dustiness of the available enzymes.

Since the introduction of enzymes into the detergent business, many developments in the granulation and coating of enzymes have been offered by the industry.

U.S. Pat. No. 4,106,991 describes an improved formulation of enzyme granules by including within the composition undergoing granulation, finely divided cellulose fibers in an amount of 2–40% w/w based on the dry weight of the whole composition. In addition, this patent describes that waxy substances can be used to coat the particles of the granulate.

U.S. Pat. No. 4,689,297 describes enzyme containing particles which comprise a particulate, water dispersible core which is 150–2,000 microns in its longest dimension, a uniform layer of enzyme around the core particle which amounts to 10%–35% by weight of the weight of the core particle, and a layer of macro-molecular, film-forming, water soluble or dispersible coating agent uniformly surrounding the enzyme layer wherein the combination of enzyme and coating agent is from 25–55% of the weight of the core particle. The core material described in this patent includes clay, a sugar crystal enclosed in layers of corn starch which is coated with a layer of dextrin, agglomerated potato starch, particulate salt, agglomerated trisodium citrate, pan crystallized NaCl flakes, bentonite granules or prills, granules containing bentonite, kaolin and diatomaceous earth or sodium citrate crystals. The film forming material may be a fatty acid ester, an alkoxylated alcohol, a polyvinyl alcohol or an ethoxylated alkylphenol.

U.S. Pat. No. 4,740,469 describes an enzyme granular composition consisting essentially of from 1–35% by weight of an enzyme and from 0.5–30% by weight of a synthetic fibrous material having an average length of from 100–500 micron and a fineness in the range of from 0.05–0.7 denier, with the balance being an extender or filler. The granular composition may further comprise a molten waxy material, such as polyethylene glycol, and optionally a colorant such as titanium dioxide.

U.S. Pat. No. 5,324,649 describes enzyme-containing granules having a core, an enzyme layer and an outer coating layer. The enzyme layer and, optionally, the core and outer coating layer contain a vinyl polymer.

WO 91/09941 describes an enzyme containing preparation whereby at least 50% of the enzymatic activity is present in the preparation as enzyme crystals. The preparation can be either a slurry or a granulate.

WO 97/12958 discloses a microgranular enzyme composition. The granules are made by fluid-bed agglomeration which results in granules with numerous carrier or seed particles coated with enzyme and bound together by a binder.

Two of the methods known for preparing granulated enzymes in fluid-bed coaters include fluid-bed agglomeration and fluid-bed spray-coating. In fluid-bed agglomeration, one or more enzymes and a binder are sprayed on to fine powdery carrier solids, which are built up in size by agglomerating together carrier particles. In these agglomerates, the binder and enzyme serve to bridge multiple carrier particles into granules of irregular size and shape. In fluid-bed spray-coating, enzyme can be layered onto uniform core particles together with an optional binder.

It would be desirable to produce enzyme granules with improved stability, particularly in bleach-containing detergents at high humidity and temperature. Current fluid-bed spray-coated enzyme granules contain the enzyme in a relatively thin layer near the surface of the granule. This geometry renders the enzyme more vulnerable to being chipped off of the granule in a concentrated layer during handling and conveying operations, increasing the likelihood and levels of airborne enzyme aerosols in the working environment. This geometry also makes the enzyme more vulnerable to attack by penetrating moisture and inactivating substances.

However, even in light of these developments offered by the industry (as described above) there is a continuing need for low-dust enzyme granules which have additional beneficial characteristics. Additional beneficial characteristics needed in the enzyme granulation industry are low-residue granule formulations (where low residue is defined as a reduced tendency to leave noticeable undissolved residues on clothes or other material), and improved stability during storage in, for example, bleach-containing detergent formulas, for example, those containing peroxygen bleaches such as sodium perborate or sodium percarbonate. Accomplishing all these desired characteristics simultaneously is a particularly challenging task since, for example, many delayed release or low-dust agents such as fibrous cellulose or kaolin leave behind insoluble residues.

As such, there is a need for, for example, a detergent enzyme granule which is simultaneously non-dusting, stable when stored in detergents, and easy to manufacture in a controlled size distribution. Granules of a controlled size distribution are desirable in order to impart good flowability properties for handling and blending into detergents, and to resist segregation and settling once formulated into detergents. A controlled particle size distribution and uniform shape of particles are also important contributors to achieving a low dust granule.

Therefore, it is an object of the present invention to provide low-dust, low residue, highly soluble enzyme granules having increased stability particularly in bleach-containing detergents. It is another object of the present invention to provide processes which afford the formation of such improved granules.

SUMMARY OF THE INVENTION

The present invention provides a granule that includes a protein core that includes a protein matrix. The protein matrix includes at least one protein (e.g., one or more enzymes) mixed together with a starch. Optionally, a barrier layer can be layered over the protein core or a barrier material can be included in the protein core. Also, optionally, a coating can be applied over the seed particle, the enzyme matrix and/or the barrier layer.

The present invention further provides a granule that includes a protein core that includes a protein matrix layered over a seed particle. The protein matrix includes at least one protein (e.g., one or more enzymes) mixed together with a starch. Optionally, a barrier layer can be layered over the enzyme core or a barrier material can be included in the enzyme core. Also, optionally, a coating can be applied over the seed particle, the enzyme matrix and/or the barrier layer.

The present invention also provides a granule that includes an enzyme core that includes an enzyme matrix. The enzyme matrix includes one or more enzymes mixed together with a starch. Optionally, a barrier layer can be layered over the enzyme core or a barrier material can be included in the enzyme core. Also, optionally, a coating can be applied over the seed particle, the enzyme matrix and/or the barrier layer.

The present invention additionally provides a granule that includes an enzyme core that includes an enzyme matrix layered over a seed particle. The enzyme matrix includes one or more enzymes mixed together with a starch. Optionally, a barrier layer can be layered over the enzyme core or a barrier material can be included in the enzyme core. Also, optionally, a coating can be applied over the seed particle, the enzyme matrix and/or the barrier layer.

The other features, aspects and advantages of the present invention will become apparent from the following detailed description, in conjunction with the appended claims.

DETAILED DESCRIPTION OF THE INVENTION

One embodiment of the invention is a granule that includes a protein core that includes a protein matrix. The protein matrix includes one or more proteins mixed together with a starch. Optionally, a barrier layer can be layered over the protein core or a barrier material can be included in the protein core. Also, optionally, a coating can be applied over the seed particle, the enzyme matrix and/or the barrier layer.

A further embodiment of the invention is a granule that includes a protein core that includes a protein matrix layered over a seed particle. The protein matrix includes one or more proteins mixed together with a starch. Optionally, a barrier layer can be layered over the protein core or a barrier material can be included in the protein core. Also, optionally, a coating can be applied over the seed particle, the enzyme matrix and/or the barrier layer.

Another embodiment of the invention is a granule that includes an enzyme core that includes an enzyme matrix. The enzyme matrix includes one or more enzymes mixed together with a starch. Optionally, a barrier layer can be layered over the enzyme core or a barrier material can be included in the enzyme core. Also, optionally, a coating can be applied over the seed particle, the enzyme matrix and/or the barrier layer.

A further embodiment of the invention is a granule that includes an enzyme core that includes an enzyme matrix layered over a seed particle. The enzyme matrix includes one or more enzymes mixed together with a starch. Optionally, a barrier layer can be layered over the enzyme core or a barrier material can be included in the enzyme core. Also, optionally, a coating can be applied over the seed particle, the enzyme matrix and/or the barrier layer.

A "protein core", an "enzyme core" or a "core" includes a protein matrix, for example, an enzyme matrix in the case of an enzyme core. The matrix can be homogenous throughout the core or can be layered over a seed particle. There can be one or more layers between the seed particle and the matrix or the matrix and the barrier layer, for example, a coating such as polyvinyl alcohol (PVA).

Seed particles are inert particles upon which the enzyme matrix can be layered which can be composed, for example, of inorganic salts, sugars, sugar alcohols, small organic molecules such as organic acids or salts, minerals such as clays or silicates or a combination of two or more of these. Suitable soluble ingredients for incorporation into seed particles include: sodium chloride, potassium chloride, ammonium sulfate, sodium sulfate, sodium sesquicarbonate, urea, citric acid, citrate, sorbitol, mannitol, oleate, sucrose, lactose and the like. Soluble ingredients can be combined with dispersible ingredients such as talc, kaolin or bentonite. Seed particles can be fabricated by a variety of granulation techniques including: crystallization, precipitation, pan-coating, fluid-bed coating, fluid-bed agglomeration, rotary atomization, extrusion, prilling, spheronization, drum granulation and high shear agglomeration. In the granules of the present invention, if a seed particle is used then the ratio of seed particles to granules is 1:1.

The "protein matrix", "enzyme matrix" or "matrix" is an admixture of one or more proteins such as an enzyme and a starch. Optionally, the matrix can include a sugar, such as sucrose. The selected components can be mixed, for example, in solution or as a slurry. The protein can be applied from a solution or applied in slurry form as a suspension of crystals or precipitated protein. The matrix of the present invention comprises between about 20–80% of the weight of the granule.

By burying a protein within a matrix, the protein can be better protected from the twin dangers of attrition and activity loss. Also, to achieve a low dusting granular protein product, it is necessary to control the shape and size distribution of the granules. Uniform and reproducible size and shape also contribute to granule stability, since particle breakup and re-agglomeration would bring some protein near the granule surface.

Surprisingly, it has been found that by combining a starch with a protein, the protein can be applied uniformly to individual seed particles at rapid rates without agglomeration or attrition. The resulting particle size distribution can be precisely controlled, based on knowledge of the starting seed size distribution and the amount of solids to be added. The resulting particles are approximately spherical in shape, have high cohesive strength, and are resistant to attrition and penetration by moisture and inactivating substances.

Starches have high water solubility or dispersibility. A matrix formula can be easily prepared which includes starches and enzymes as a solution or slurry with high total solids concentration. Total solution or slurry solids concentrations of 20–50% w/w or more can be formulated. These concentrated mixtures are highly desirable in that they can be formed into granules with a minimal need for evaporating water, an advantage in any granulation and drying process.

Proteins that are within the scope of the present invention include pharmaceutically important proteins such as hormones or other therapeutic proteins and industrially important proteins such as enzymes.

Any enzyme or combination of enzymes may be used in the present invention. Preferred enzymes include those enzymes capable of hydrolyzing substrates, e.g. stains. These enzymes are known as hydrolases which include, but are not limited to, proteases (bacterial, fungal, acid, neutral or alkaline), amylases (alpha or beta), lipases, cellulases and mixtures thereof. Particularly preferred enzymes are subtilisins and cellulases. Most preferred are subtilisins such as described in U.S. Pat. No. 4,760,025, EP Patent 130 756 B1 and EP Patent Application WO 91/06637, which are incorporated herein by reference, and cellulases such as Multifect L250™ and Puradax™, commercially available from Genencor International. Other enzymes that can be used in the present invention include oxidases, transferases, dehydratases, reductases, hemicellulases and isomerases.

The matrix of the granules of the present invention may further comprise one or more synthetic polymers or other excipients as known to those skilled in the art. Suitable synthetic polymers include polyethylene oxide, polyvinyl alcohol, polyvinyl pyrrolidone, polyethylene glycol and polyethylene oxide/polypropylene oxide.

The matrix may also further comprise plasticizers and anti-agglomeration agents. Suitable plasticizers useful in the present invention include polyols such as glycerol, propylene glycol, polyethylene glycol (PEG), urea, or other known plasticizers such as triethyl citrate, dibutyl or dimethyl phthalate or water. Suitable anti-agglomeration agents include fine insoluble or sparingly soluble materials such as talc, $TiO_2$, clays, amorphous silica, magnesium stearate, stearic acid and calcium carbonate.

The granules of the present invention can further comprise a barrier layer. A barrier layer is used to slow or prevent the diffusion of substances that can adversely affect the protein or enzyme into the matrix. The barrier layer is made up of a barrier material and can be coated over the protein core or the barrier material can be included in the protein core. Suitable barrier materials include, for example, inorganic salts or organic acids or salts.

The granules of the present invention can also comprise one or more coating layers. For example, such coating layers may be one or more intermediate coating layers or such coating layers may be one or more outside coating layers or a combination thereof. Coating layers may serve any of a number of functions in a granule composition, depending on the end use of the enzyme granule. For example, coatings may render the enzyme resistant to oxidation by bleach, bring about the desirable rates of dissolution upon introduction of the granule into an aqueous medium, or provide a barrier against ambient moisture in order to enhance the storage stability of the enzyme and reduce the possibility of microbial growth within the granule.

Suitable coatings include water soluble or water dispersible film-forming polymers such as polyvinyl alcohol (PVA), polyvinyl pyrrolidone (PVP), cellulose derivatives such as methylcellulose, hydroxypropyl methylcellulose, hydroxycellulose, ethylcellulose, carboxymethyl cellulose, hydroxypropyl cellulose, polyethylene glycol, polyethylene oxide, gum arabic, xanthan, carrageenan, chitosan, latex polymers, and enteric coatings. Furthermore, coating agents may be used in conjunction with other active agents of the same or different categories.

Suitable PVAs for incorporation in the coating layer(s) of the granule include partially hydrolyzed, fully hydrolyzed and intermediately hydrolyzed PVAs having low to high degrees of viscosity. Preferably, the outer coating layer comprises partially hydrolyzed PVA having low viscosity. Other vinyl polymers which may be useful include polyvinyl acetate and polyvinyl pyrrolidone. Useful copolymers include, for example, PVA-methylmethacrylate copolymer and PVP—PVA copolymer.

The coating layers of the present invention may further comprise one or more of the following: plasticizers, extenders, lubricants, pigments, and optionally additional enzymes. Suitable plasticizers useful in the coating layers of the present invention are plasticizers including, for example, polyols such as sugars, sugar alcohols, or polyethylene glycols (PEGs), urea, glycol, propylene glycol or other known plasticizers such as triethyl citrate, dibutyl or dimethyl phthalate or water. Suitable pigments useful in the coating layers of the present invention include, but are not limited to, finely divided whiteners such as titanium dioxide or calcium carbonate or colored pigments and dyes or a combination thereof. Preferably such pigments are low residue pigments upon dissolution. Suitable extenders include sugars such as sucrose or starch hydrolysates such as maltodextrin and corn syrup isolids, clays such as kaolin and bentonite and talc. Suitable lubricants include nonionic surfactants such as Neodol, tallow alcohols, fatty acids, fatty acid salts such as magnesium stearate and fatty acid esters.

Adjunct ingredients may be added to the enzyme granules of the present invention. Adjunct ingredients may include: metallic salts; solubilizers; activators; antioxidants; dyes; inhibitors; binders; fragrances; enzyme protecting agents/scavengers such as ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, proteins such as bovine serum albumin, casein and the like etc.; surfactants including anionic surfactants, ampholytic surfactants, nonionic surfactants, cationic surfactants and long-chain fatty acid salts; builders; alkalis or inorganic electrolytes; bleaching agents; bluing agents and fluorescent dyes and whiteners; and caking inhibitors.

For granules having a matrix that includes, in addition to starch, a sugar (such as sucrose), it may be desirable to keep the sugar content of the matrix very low (e.g., substantially less than the starch content). For example, in a particular spray coating process, similar to that described in the examples below, amylase granules having a 1:1 corn starch-:sucrose matrix were found to be very tacky and had a tendency to agglomerate during the spray cycle. A drastic reduction in the sucrose content alleviated the tackiness of the matrix. Accordingly, in certain circumstances, it is preferred to employ a matrix having a high starch content relative to the sucrose content. In one preferred embodiment, the ratio (w/w) of starch to sucrose is much greater than 1:1, e.g., in the range of about 5:1 to 15:1. For example, the ratio can be about 10:1.

In an exemplary formulation, sucrose is present in the matrix in an amount of from about 0.5% (w/w) to about 8% (w/w), relative to the total weight of the granules; and preferably in an amount of about 2% (w/w). In one particularly preferred embodiment, corn starch is present in the matrix in an amount of about 23% and sucrose is present in the matrix in an amount of about 2% (again, w/w, relative to the total weight of the granules). The sucrose content of this embodiment can be increased above 2%, but preferably should not exceed equal parts of corn starch. For example, for every 1% increase of sucrose added to the matrix, an equal amount of corn starch is subtracted from the matrix. Thus, if the sucrose content is increased from 2% up to 5%, the corn starch content would be adjusted down from 23% to 20%. In this example, the maximum sucrose content would be 12.5%, equaling the calculated corn starch content.

While little or no sugar may be useful in certain circumstances (e.g., as just discussed), it should be appreciated that other circumstances (e.g., where agglomeration does not present a significant problem) may call for a higher sugar content in the matrix.

The granules described herein may be made by methods known to those skilled in the art of enzyme granulation, including pan-coating, fluid-bed coating, prilling, disc granulation, spray drying, extrusion, centrifugal extrusion, spheronization, drum granulation, high shear agglomeration, or combinations of these techniques.

The following examples are representative and not intended to be limiting. One skilled in the art could choose other enzymes, matrices, seed particles, methods and coating agents based on the teachings herein.

EXAMPLES

Example 1

Pilot Scale Fluid Bed Spray Coating of Amylase/ Starch Matrix 26 kg sucrose crystals sieved to between 35 and 50 mesh were charged into Deseret 60 fluid bed coater and fluidizer. 15.3 kg of an aqueous amylase solution with 31% total dry solids and 12.5% w/w active amylase was added to 43.5 kg of an aqueous solution containing 23.5 kg of corn starch. The combined solution was sprayed onto the sucrose under the following conditions:

| Fluid feed rate | 0.8 kg/min |
| Atomization pressure | 75 psi |
| Inlet air temperature set point | NA |
| Product temperature set point | 45° C. |
| Inlet air rate | 1300 cfm |

The coated particles were then coated with an aqueous solution containing 66.7 kg (40% w/w) of magnesium sulfate heptahydrate. This coating was applied under the following conditions:

| Fluid feed rate | 1.1 kg/min |
| Atomization pressure | 60 psi |
| Inlet air temperature set point | NA |
| Product temperature set point | 47° C. |
| Inlet Air rate | 1800 cfm |

The magnesium sulfate coated particles were then cosmetically coated with 92.6 kg of an aqueous solution containing 7.1 kg (6.2% w/w) titanium dioxide, 2.9 kg (2.5% w/w) methylcellulose, 2.9 kg (2.5%) Purecote B790, 1.2kg (1.5% w/w) Neodol 23/6.5, and 2.0 kg (1.67% w/w) of polyethylene glycol at a MW of 600. The cosmetic coating was applied under the following conditions:

| Fluid feed rate | 0.5 kg/min |
| Atomization pressure | 75 psi |
| Inlet air temperature set point | NA |
| Product temperature set point | 47° C. |
| Inlet Air rate | 1800 cfm |

Example 2

Pilot Scale Fluid Bed Spray Coating of Amylase/ Sucrose-Starch Matrix 26 kg sucrose crystals sieved to between 35 and 50 mesh were charged into Deseret 60 fluid bed coater and fluidizer. 15.3 kg of an aqueous amylase solution with 31% total dry solids and 12.5% w/w active amylase was added to 59.3 kg of an aqueous solution containing 7.8 kg of sucrose and 23.5 kg of corn starch. The combined solution was sprayed onto the sucrose under the following conditions:

| Fluid feed rate | 0.8 kg/min |
| Atomization pressure | 75 psi |
| Inlet air temperature set point | NA |
| Product temperature set point | 45° C. |
| Inlet air rate | 1300 cfm |

The MgSO4 and cosmetic coating were run exactly as described above in Example 1.

Example 3

Exemplary Amylase Granule Formulations

Two additional Lots, denoted as 39 and 43, were prepared substantially in accordance with the just-described procedures. Pertinent aspects of the formulations for the granules of Lots 39 and 43 were as follows:

The protein matrix of Lot 39 had a 5000 unit payload (wherein "unit" refers to TAU/g [see, e.g., U.S. Pat. No. 5,364,782]). Corn starch was present in the matrix in an amount of about 18.8% (w/w), relative to the total weight of the granules. The protein maxtrix of this lot was substantially devoid of sucrose. A second layer comprising magnesium sulfate heptahydrate was coated over the protein matrix, such that 30% of the granular weight was comprised of $MgSO_4.7H2O$.

The matrix of Lot 43 had the same payload as in Lot 39. Corn starch was present in the matrix in an amount of about 18.8% (w/w), and sucrose was present in the matrix in an amount of about 6.2% (w/w), both relative to the total weight of the granules. As with the granules of Lot 39, a second layer comprising magnesium sulfate heptahydrate was coated over the protein matrix, such that 30% of the granular weight was comprised of $MgSO_4.7H2O$.

Example 4

Accelerated Stability Tests using a Detergent Base

The granules of Example 3 were analyzed to determine their stability in accelerated stability tests. The methods for these procedures were substantially as described in Example 3 of WO 99/32613, incorporated herein by reference.

As discussed in WO 99/32613, the accelerated stability test is designed to aid in the development and screening of granular formulations, as it provides an accelerated means of determining relative granule stability. The conditions of the accelerated stability test (AST) are far more severe than enzyme granules or detergents would encounter in realistic storage or transport. The AST is a "stress test" designed to discriminate differences between formulations which would otherwise not be evident for weeks or months.

The AST results set out in Table 2, below, show the percent activity remaining for each of Lots 39 and 43, over a four day period.

TABLE 2

| | Percent Activity of the Original | | |
|---|---|---|---|
| | Day 0 | Day 1.3 | Day 4 |
| Lot 39 | 100.0 | 94.3 | 89.3 |
| Lot 43 | 100.0 | 94.4 | 86.9 |

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

It is claimed:

1. A granule comprising an admixture of protein, corn starch and sugar layered over an inert particle wherein the ratio (w/w) of corn starch to sugar is greater than 1:1.

2. The granule of claim 1 further comprising a coating layer between the inert particle and the admixture.

3. The granule of claim 1 further comprising a coating layer over the admixture.

4. The granule of claim 3, wherein the coating is selected from the group consisting of polyvinyl alcohol, polyvinyl pyrrolidone, cellulose derivatives such as methylcellulose, hydroxypropyl methylcellulose, hydroxycellulose, ethylcellulose, carboxymethyl cellulose, hydroxypropyl cellulose, polyethylene glycol, polyethylene oxide, chitosan, gum arabic, xanthan and carrageenan.

5. The granule of claim 1, wherein the sugar content is no more than about 8% w/w based on the weight of the granule.

6. The granule of claim 5, wherein the sugar content is within the range of from about 0.5% to about 3% w/w based on the weight of the granule.

7. The granule of claim 6, wherein the sugar content is about 2% w/w based on the weight of the granule.

8. The granule of claim 5, wherein the sugar is sucrose.

9. The granule of claim 1, wherein the protein is an enzyme.

10. The granule of claim 9, wherein the enzyme is selected from the group consisting of protease, amylase, lipase and cellulase.

11. A granule comprising an admixture layered over an inert particle, the admixture consisting essentially of: (i) an enzyme, (ii) a corn starch, and (iii) a sugar, wherein the sugar content is no more than about 8% w/w based on the weight of the granule.

12. The granule of claim 11, wherein the sugar content is between about 1–3% w/w based on the weight of the granule.

13. A granule comprising an inert particle layered over with an admixture of (i) an enzyme, (ii) a corn starch, and (iii) a sugar wherein the ratio of corn starch to sugar is at least about 5:1.

14. The granule of claim 13, wherein the ratio of starch to sugar is within a range of about 5:1 to about 15:1.

15. The granule of claim 14, wherein the ratio of starch to sugar is about 10:1.

16. The granule of claim 13, wherein the sugar is sucrose.

17. A granule comprising an inert particle layered over with an admixture of (i) an enzyme selected from the group consisting of proteases, cellulases, amylases, and lipases, (ii) a corn starch, and (iii) sucrose, wherein the enzyme is embedded in a mixture of the starch and sucrose and the ratio of corn starch to sucrose is within the range of about 5:1 to about 15:1.

* * * * *